United States Patent [19]

Jolly

[11] Plant 4,564

[45] Jul. 8, 1980

[54] ROSE PLANT

[75] Inventor: Nelson F. Jolly, Galena, Md.

[73] Assignee: Chattem, Inc., Chattanooga, Tenn.

[21] Appl. No.: 17,567

[22] Filed: Mar. 5, 1979

[51] Int. Cl.[2] ..... A01H 5/00

[52] U.S. Cl. ..... Plt./10

[58] Field of Search ..... Plt./10, 7

*Primary Examiner*—Robert E. Bagwill

*Attorney, Agent, or Firm*—Vincent G. Gioia

[57] ABSTRACT

The present invention relates to a new and distinct variety of rose plant of the miniature rose class, which was originated by my crossing as seed parent the floribunda rose known as "Orange Sensation" and the miniature rose known as "Zinger" as pollen parent.

1 Drawing Figure

1

Among the novel characteristics possessed by this new variety which distinguish it from its parents and all other varieties of which I am aware are: (1) long lasting blooms of unusually clean orange red coloring borne primarily one to a stem or in small clusters of two to three flowers but in large quantities on a very floriferous plant and (2) a compact, vigorous uniform branching plant with abundant, deep green foliage. Asexual reproduction by budding of the new variety as performed in Kent County, Md. shows that the foregoing and other distinguishing characteristics come true to form and are established and transmitted through succeeding propagations.

The new and improved rose variety which I have developed is an unusally pure orange red color break in a miniature rose that maintains its coloring from bud to mature bloom and also upon aging. This constancy of coloring is unusual in miniature roses and especially in the orange red color class. The flowers are many-petalled and start ovoid, then become flat upon opening. Because the petals overlap in shingle-like formation the effect is a beautiful orange colored floret which in the aggregate produce a very attractive orange-red mass of color due to the general tonality from a distance. An additional particularly desirable and distinguishing characteristic of my new variety is the especially long lasting blooms which endure as long as two to three weeks on the plant and seven to eight days as a cut flower.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "33A" is plate 33A of the Royal Horticultural Society Color Chart.

Parentage: Seedling.

*Seed parent.*—"Orange Sensation".

*Pollen parent.*—"Zinger".

Class: Miniature.

The following observations are made of specimens grown outdoors in Kent County, Md., during the month of September.

2

FLOWER

Blooming habit: Continuous, very floriferous.

A. Bud:

(1) *Size.*—Small.

(2) *Form.*—Ovoid.

(3) *Color.*—Bud color when the sepals first divide, and they unfurl and when half blown is a constant orange red 33A. The underside of the petals sometimes tends to red 39A.

(4) *Peduncle.*—Length — 5 to 5½ cm. Aspect — smooth. Stength — medium, straight. Color — yellow green 144A.

B. Bloom:

(1) *Size.*—Average size when fully expanded — about 1-11/16 inches.

(2) *Borne.*—One to a stem or 2 to 3 together.

(3) *Form.*—Ovoid becoming flat at maturity.

(4) *Petalage.* —Number of petals under normal conditions — about 35 to 38.

(5) *Color.*—During first two days. Upper surface of petals is orange red 33A except at point of attachment where color tends to be yellow 6C. The underside of petals tends to be slightly darker orange red shading 33B. The general tonality from a distance is a clean orange red.

(6) *Color change as bloom ages.*—The orange red coloring and general tonality is maintained on aging even after three or more days.

C. Petals.:

(1) *Texture.*—Medium.

(2) *Appearance.*—Satiny.

(3) *Form.*—Oval, nearly round, coming to point at tips.

(4) *Arrangement.*—Regularly arranged, shingle-like overlay.

(5) *Petaloids in center.*—Few (2-5).

(6) *Persistence.*—Drop off cleanly.

(7) *Fragrance.*—Slightly fruity.

(8) *Lasting quality.*—Very lasting (2-3 weeks) on the plant and as a cut flower (7-8 days).

REPRODUCTIVE ORGANS

A. Stamens, filaments and anthers:

(1) *Arrangement.*—Regularly arranged around styles.

(2) *Color.*—Yellow orange 15A.

B. Pollen: Color — yellow orange 22A.

C. Styles: Bunched, regular, even arrangement.

D. Stigmas: Color — top is yellow orange 23D and staff is red purple 57D.

E. Hips: None.

PLANT

A. Form: Compact.

B. Growth: Vigorous, uniform branching.

*Height attained.*—14 to 16 inches.

C. Foliage: Compound 5 and 7 leaflets.

(1) *Size.*—Medium.

(2) *Quantity.*—Abundant.

(3) *Color.*—New foliage: Upper side — yellow green 146A. Under side — greyed orange 176A. Old foliage: Upper side — green 137A. Under side — grey green 191A.

(4) *Shape.*—Oval, pointed.

(5) *Texture.*—Upper side — smooth. Under side — smooth, dull.

(6) *Edge.*—Serrated.

(7) *Serration.*—About 8 serrations per cm.

(8) *Leaf stem.*—Color — near to yellow green 144A. Under side — near to yellow green 146B.

(9) *Stipules.*—¼-cm. long, sharp, pointed.

(10) *Resistance to disease.*—Blackspot — normal. Mildew — some observed.

D. Wood:

(1) *New wood.*—Color — greyed orange 165A to green 138B. Bark — Smooth.

(2) *Old wood.*—Color — green 138A. Bark — smooth.

E. Thorns:

(1) *Thorns.*—Quantity — ordinary. Form — flat, slightly hooked. Length — short. Color — greyed orange 173A. Position — irregular.

(2) *Prickles.*—None.

I claim:

1. A new and distinct variety of rose plant of the miniature class, substantially as shown and described, characterized particularly by flowers of unusually constant orange red coloring which are very long lasting on the plant, up to 2 to 3 weeks, and as cut flowers, up to 7 to 8 days, and a vigorous, compact growing plant that blooms profusely.

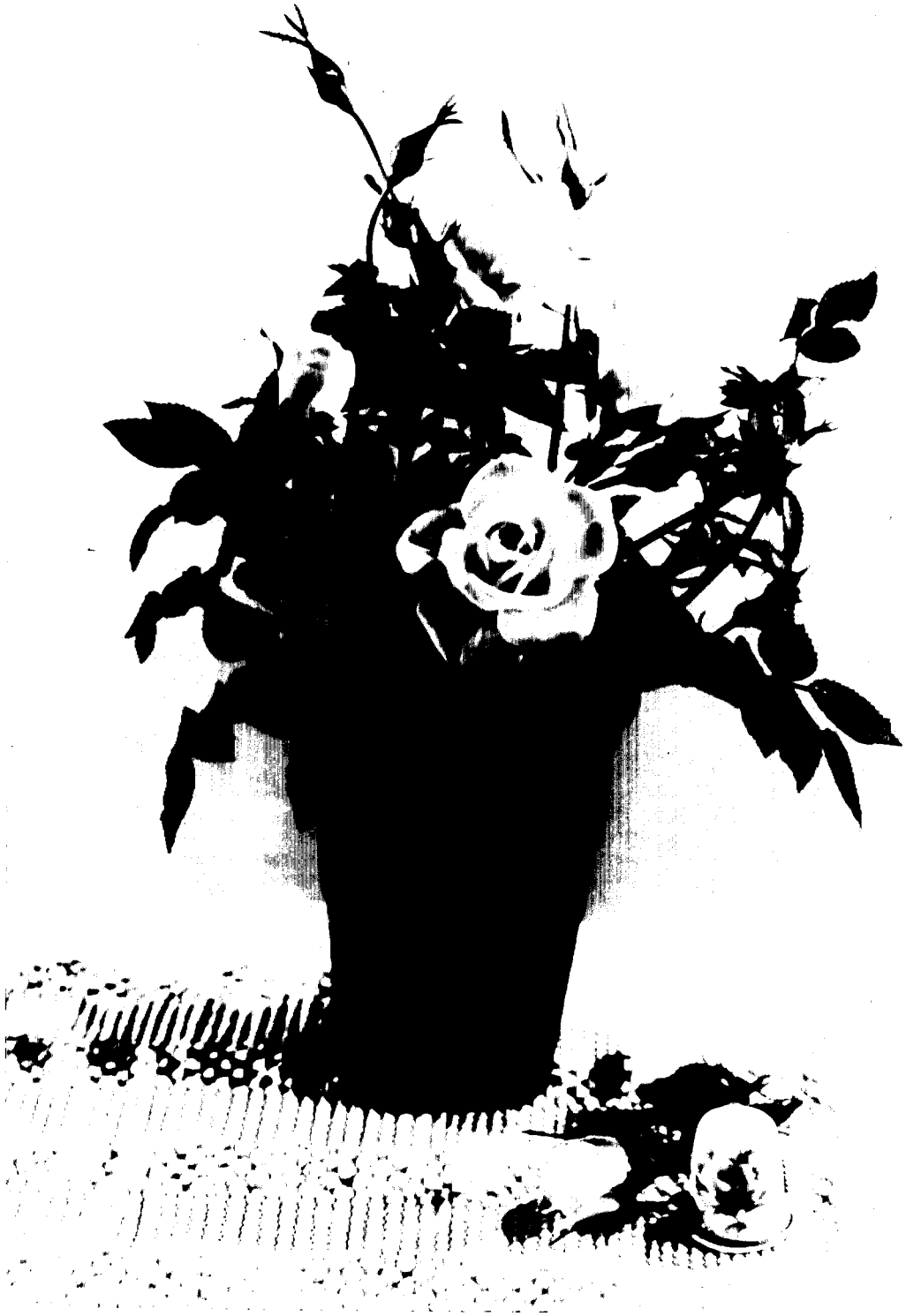

* * * * *